United States Patent
Shih et al.

[19]

[11] Patent Number: 5,984,868
[45] Date of Patent: Nov. 16, 1999

[54] DEVICE FOR MEASURING AN ABSORBED DOSE OF GAS BY SKIN AND METHOD THEREFOR

[75] Inventors: Tung-Sheng Shih, Taipei; Peng-Yau Wang, Hsin-Ying, both of Taiwan

[73] Assignee: Institute of Occupational Safety and Health, Council of Labor Affairs, Executive Yuan, Taipei, Taiwan

[21] Appl. No.: 09/105,990

[22] Filed: Jun. 29, 1998

[51] Int. Cl.[6] ..................................................... A61N 5/00
[52] U.S. Cl. ........................... 600/300; 600/345; 604/19; 128/897; 128/898
[58] Field of Search ..................................... 600/300–301, 600/345, 587, 560–561; 128/897–898

[56] References Cited

U.S. PATENT DOCUMENTS

| | | | |
|---|---|---|---|
| 5,209,919 | 5/1993 | Turteltaub et al. | 600/300 |
| 5,366,721 | 11/1994 | Turteltaub et al. | 600/300 |
| 5,376,355 | 12/1994 | Turteltaub et al. | 600/300 |

Primary Examiner—Cary O'Connor
Assistant Examiner—Michael Astorino
Attorney, Agent, or Firm—Bacon & Thomas

[57] ABSTRACT

A device is intended to measure an absorbed dose of a hazardous gas by skin of a human body and is composed of an exposure chamber, a gas concentration control system, and one or more gas sensors. A naked part of the human body is held in the exposure chamber containing the hazardous gas of a concentration which is kept in a predetermined range by the gas concentration control system. As the concentration of the hazardous gas drops below the predetermined range, the gas concentration control system replenishes the exposure chamber with an amount of the hazardous gas with the help of a concentration signal transmitted from the sensors, so that the concentration of the hazardous gas is once again kept in the predetermined range. The absorbed dose of the hazardous gas by skin is computed on the basis of the amount of the hazardous gas that is replenished.

12 Claims, 11 Drawing Sheets

DEVICE FOR MEASURING AN ABSORBED DOSE OF GAS BY SKIN AND METHOD THEREFOR

FIELD OF THE INVENTION

The present invention relates generally to a device and a method for measuring an absorbed dose of gas by skin, and more particularly to a method and a device for measuring an absorbed dose of a harmful gas by skin in an exposure chamber in which the concentration of the harmful gas can be controlled.

BACKGROUND OF THE INVENTION

The research papers dealing with the skin absorption of a harmful gas and vapor are few and far between in view of the fact that the evaluation technique used in such research is still in its infancy. The isotopic measuring technique may be employed in such research; nevertheless it is economically prohibitive and hazardous to human life. In addition, the test solutions for the isotopic measuring technique can not be easily obtained (Hefner R E, Watanabe P G, Gehring P J. Percutaneous absorption of vinyl chloride. Toxicol. Appl. Pharmacol. 34: 529–532 (1975); Hursh J B, Clarkson T W, Goldsmith L A. Percutaneous absorption of mercury vapor by man. Arch. Environ. Health 44(2): 120–127 (1989); Corley R A, et al., Foundam. Appl. Toxicol., 39: 120–130 (1997)).

Tsuruta disclosed a method in which a mouse was anesthetized with pentabarbital and was then placed in a dynamic chamber. Immediately after being exposed to the standard gas in the dynamic chamber, the mouse was frozen by the liquid nitrogen prior to being crushed. A portion of the crushed remains of the mouse was removed and weighed. A mouse extract was obtained by a quantitative solvent. The total amount of the absorbed dose of the standard gas by the mouse was measured by gas phase chromatography (Tsuruta H. Skin absorption of organic solvent vapors in nude mice in vivo. Ind. Health 27: 37–47 (1989): Tsuruta H., et al., Ind. Health, 22: 219–212 (1984); Tsuruta H., et al., Ind. Health, 25: 215–220 (1987)). In spite of the fact that the Tsuruta's method can be carried out with precision, it can not be used to investigate the absorbed dose of the standard gas by the human body in light of tediousness and offensiveness of the method.

Currently, the most commonly used method of toxicological dynamics involves an animal or human subject, which is exposed to the standard gas in a dynamic chamber or closed exposure chamber for several hours. Thereafter, the samples are taken continuously from the subject for testing the concentration of the harmful substance or the metabolite contained in the subject's blood or tissues. The absorbed dose of the harmful substance by the subject's skin is determined by inference in conjunction with the computer model of toxicological dynamics and some hypotheses (Piotrowski J., Br. J. Ind. Med., 24: 60–65 (1967); McDougal J N., Toxicol Appl. Pharmacol., 85: 286–294 (1986)). The closed exposure chamber is defective in design in that it can not provide a stable exposure concentration, and that the control of temperature and humidity in the chamber can not be accounted for. On the other hand, the dynamic exposure chamber is capable of providing a stable exposure concentration, temperature, humidity, or wind velocity; nevertheless, it is incapable of measuring an actually absorbed dose of the gas. In addition, the dynamic exposure chamber is not cost-effective in light of a large amount of waste gas it produces. In other words, additional costly equipment is called for to deal with the waste gas. Theoretically, the absorbed dose of a substance by the skin of a subject is equal to the sum of the absorbed doses of the substance by the blood, the tissues, the organs, and the metabolite of the subject. The drawback of such a method is that the method involves a number of parameters, such as the distribution coefficients of the blood and the tissue which are derived from the data obtained from the animal experiments. In addition, the standard samples can not be easily obtained in view of the fact that the metabolites of different animals are various, and that the absorbed substance may be combined with the protein. Moreover, it is difficult to investigate the change in the absorption rate of the skin, or to know whether the absorption rate of the skin reaches saturation, during the time when the skin is exposed to the substance under investigation. This may explain the reason why there is only a limited number of articles related to the skin absorption of gas can be found (Fiber J G., et al., Arch. Toxicol., 47: 279–292 (1981); McDougal J N, Jepson G W, Clewell H J. Anderson M E. Dermal absorption of dihalomethane vapors. Toxicol. Appl. Pharmacol. 79: 150–158 (1985).; Gargas M L., Toxicol. Appl. Pharmacol., 86: 341–352 (1986)). A method for direct measurement of the absorbed dose of a substance by the animal skin has never been disclosed so far.

SUMMARY OF THE INVENTION

The primary objective of the present invention is therefore to provide a method and a device for measuring the absorbed dose of a substance by the skin. The system of the present invention is based on the principle of mass conservation in conjunction with the concept of the automatic control of the waste water treatment, and is composed of an automatic feedback control system capable of maintaining a constant exposure concentration of a harmful substance in the exposure chamber such that the absorbed dose of the harmful substance by the skin is equal to the dose of the harmful substance which is added to the exposure chamber to maintain the constant concentration of the harmful substance in the exposure chamber.

The device of the present invention is provided with an exposure chamber, a gas concentration control system, and a gas sensor. The method of the present invention is intended to measure the absorbed dose of the gas by the skin by employing the device of the present invention.

The foregoing objective, features and functions of the present invention will be more readily understood upon a thoughtful deliberation of the following detailed description of the present invention with reference to the accompanying drawings.

DETAILED DESCRIPTION OF THE INVENTION

The device of the present invention for measuring an absorbed dose of gas by the skin is composed of an exposure chamber, a gas concentration control system, and one or more sets of gas sensors.

The exposure chamber is intended to contain the gas and an animal or human body for measuring an absorbed dose of the gas by the skin of the animal or human body. The exposure chamber is connected with the gas concentration control system for regulating the concentration of the gas contained in the exposure chamber. The concentration of the gas contained in the exposure chamber is monitored by the gas sensor having a detection body and a signal output end. The detection body is located in the exposure chamber, whereas the signal output end is connected with the gas concentration control system. The gas sensor is capable of detecting the gas concentration and of generating a concentration signal, which is transmitted to the gas concentration control system.

The present invention includes a method for implementing the measurement of an absorbed dose of the gas by the skin by using the device of the present invention.

It must be noted here that the animal or human body used in the present invention as a subject may be a part or whole of a trunk of the animal or the human being.

The exposure chamber of the present invention is not limited in shape and size, depending on the shape and the size of the subject. For example, if the subject is an entire human body, the exposure chamber may be constructed such that it is provided with a door through which the subject can enter or exit the exposure chamber, and that the exposure chamber is hermetically sealed at such time when the door is closed. If the trunk is a human limb, such as a hand, the exposure chamber may be provided with an entry port to enable the hand to extend into the exposure chamber. In the meantime, the entry port should be provided with an airtight mechanism capable of sealing the exposure chamber hermetically at the time when the hand is extended into the exposure chamber. The airtight mechanism is formed of a Velcro® strap, a fastening strap or an inflatable loop bag in conjunction with a cushion pad.

The gas referred to above is gas or vapor hazardous to the human body in accordance with the definitions set forth by OSHA (Occupational Safety and Health Administration) and EPA (Environmental Protection Agency). The gas sensor is specifically designed in light of the nature of the gas to be tested. For example, if the gas is 2-methoxy ethanol vapor, the gas sensors sold under code names of TGS800 and TGS822 by Figaro Company are suggested.

The gas concentration control system of the present invention is similar in construction to the prior art control system. If necessary, additional control systems may be added. The control system used in the present invention is composed of a personal computer which is externally connected with an analog-to-digital converter (ADC) interface card and is then connected with the gas sensor for receiving the concentration signal of a hazardous gas contained in the exposure chamber. Upon completion of calculation done by the personal computer, a control signal is transmitted from a digital output (DO) end of the analog-to-digital converter (ADC) interface card. For example, the entry of the trunk into the exposure chamber results in a decrease in the concentration of the hazardous gas contained in the exposure chamber. Whenever the concentration of the hazardous gas detected by the gas sensor (such as TGS800) drops below the control concentration, a concentration signal is transmitted from the gas sensor to the personal computer via ADC. Upon completion of the calculation by the personal computer, an instruction is sent out from the digital output (DO) end of the ADC such that the hazardous gas (such as 2-methoxy ethanol vapor) is injected into the exposure chamber so as to keep the concentration of the hazardous gas to remain in a predetermined range (such as 23 ppm to 27 ppm). Depending on the characteristics of the hazardous gas and the gas sensor, additional control systems may be added. For example, if the gas sensor TGS800 is used to detect the hazardous vapor of 2-methoxy ethanol, a humidity control system should be added to minimize the effect of humidity on the gas sensor TGS800. The present invention makes use of a relative humidity sensor to monitor the relative humidity of the exposure chamber in view of the fact the perspiration of the trunk located in the exposure chamber can result in an increase in the relative humidity of the exposure chamber. A suitable relative humidity sensor is available from the market, for example. model No. of Humitter 50Y sold by Vaisala Inc., MA. When the relative humidity of the exposure chamber exceeds the limit, a relative humidity signal is transmitted from the relative humidity sensor to the personal computer (PC) via the ADC. After a calculation is completed by PC, an instruction is sent out from the DO of the ADC to the humidity control system so as to lower the humidity of the exposure chamber to an acceptable level. The humidity control system comprises a dehumidifier capable of removing the moisture from the exposure chamber. On the other hand, when the relative humidity of the exposure is excessively low, the signal is transmitted from the relative humidity sensor to the PC via the ADC. After a calculation is done by PC, an instruction is sent from the DO of the ADC to the humidity control system such that the humidity of the exposure chamber is increased to an acceptable level. The humidity control system further comprises a humidifier capable of adding moisture to the exposure chamber.

The method of the present invention includes a first step in which a subject is exposed in an airtight exposure chamber containing a hazardous gas. The hazardous gas has a concentration which is regulated by a hazardous gas concentration control unit. The concentration of the hazardous gas contained in the exposure chamber is monitored by one or more gas sensors. In addition, the exposure chamber may be provided with a temperature controller and a relative humidity controller. The temperature controller consists of a conventional electrothermal controller in conjunction with a temperature sensor, such as a thermal couple. The control of humidity of the exposure chamber is thus attained by the temperature control in conjunction with the relative humidity control.

The device of the present invention will be more readily understood upon a thoughtful deliberation of the following detailed description of the preferred embodiment of the present invention.

Figure 1:
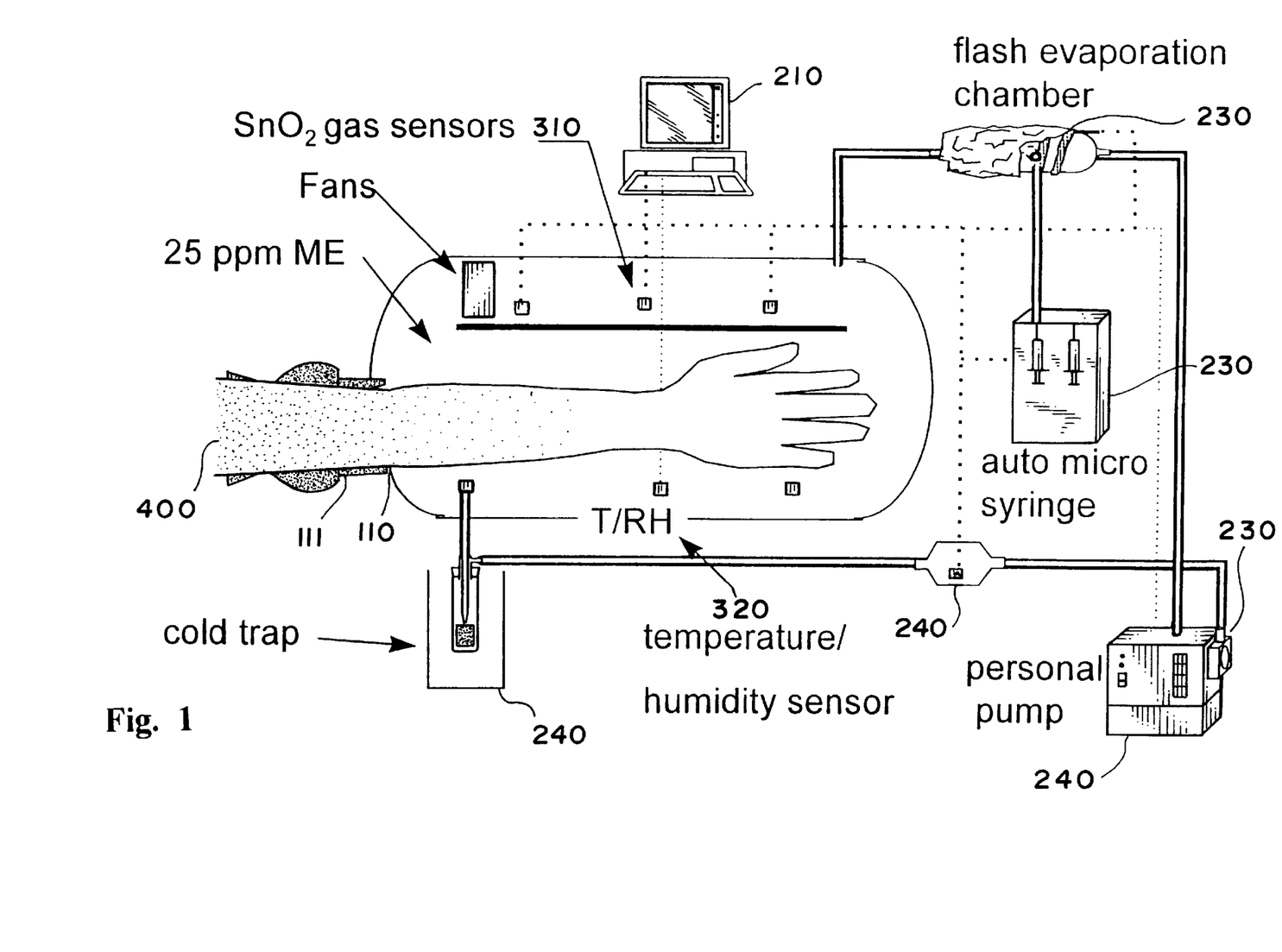
FIG. 1 shows a schematic view of a preferred embodiment of the present invention.

As shown in FIG. 1, the device of the present invention comprises an exposure chamber 100, a gas concentration control system, a gas sensor 310, and a relative humidity sensor 320. The exposure chamber 100 is provided with an entry port 110 via which a hand 400 can be extended into the exposure chamber 100 in an airtight manner. The exposure chamber 100 is further provided with a soft pad 111.

The gas concentration control system contains a hazardous gas generating unit 230, a relative humidity control unit 240, a personal computer (PC) 210, and analogdigital converter (ADC) interface card (not shown in the drawing) mounted inside the PC. The analog-digital converter (ADC) interface card includes an analog-to-digital converter and a digital output end.

Figure 3:
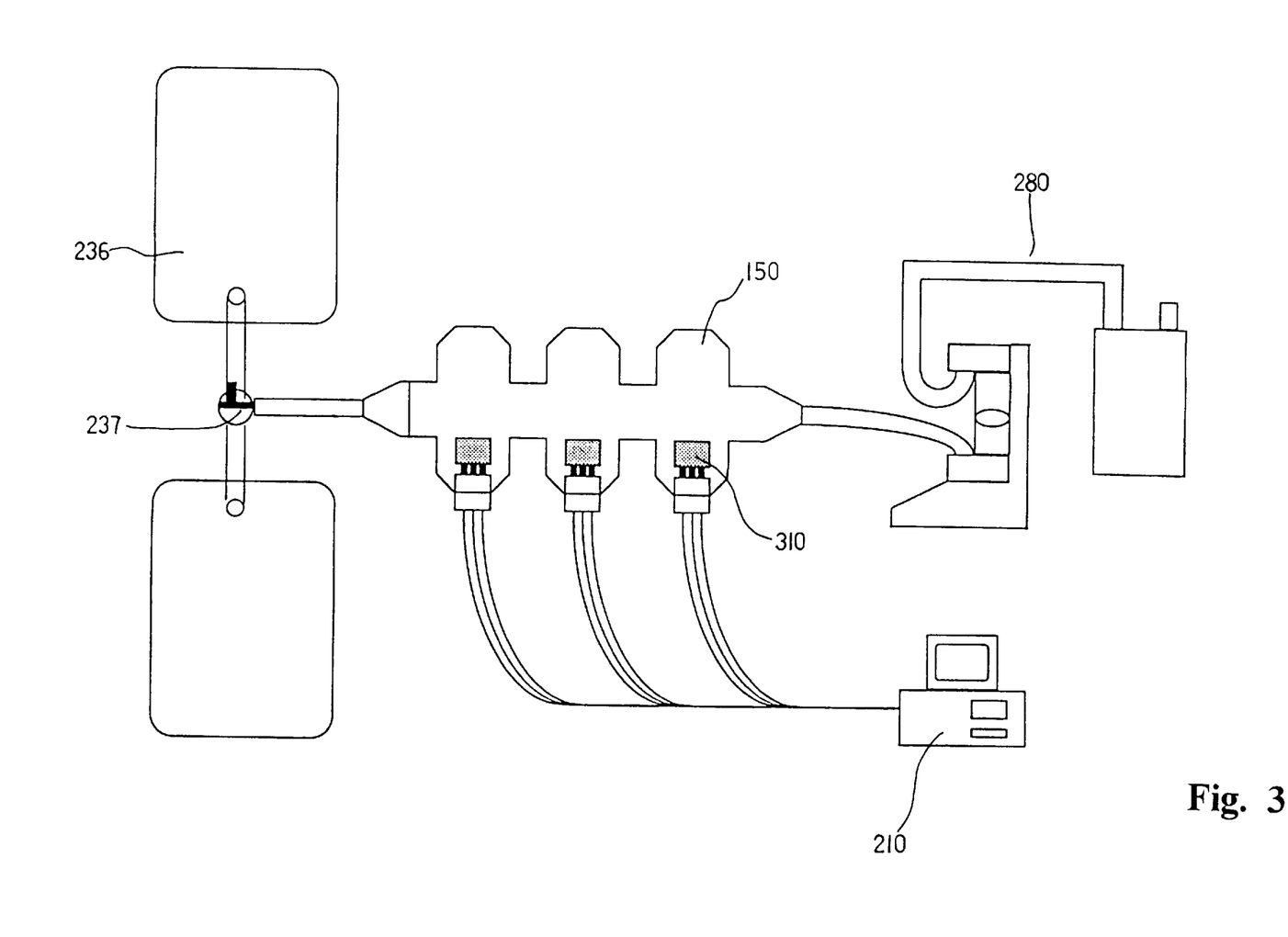
FIG. 3 shows a schematic view of a preparatory work of the preferred embodiment of the present invention as shown in FIG. 1.

FIG. 3 shows an experiment layout for testing the gas sensors 310 which are mounted in a glass exposure chamber 150. Two trapping bags 235 and 236 containing known concentrations of 2-methoxy ethanol vapor are selectively communicated with the glass exposure chamber 150 via a three-way valve 237, which simulate the hazardous gas generating unit 230 in FIG. 1. A pump together with a flow meter 280 are used to withdraw the 2-methoxy ethanol vapor from the trapping bag 235 or 236 to the glass exposure chamber 150. The personal computer (PC) 210 is used to analyze the output signals collected from the gas sensors 310.

The preferred embodiment of the present invention was implemented by using 1) a stainless steel polished exposure chamber; 2) an instant gas detector ($SnO_2$ gas sensor, model No. CS-6000-5cL, Fubata Co., Hsinchu, Taiwan); 3) a humidity control system; 4) a software and hardware systems for processing the signals related to the sensor; 5) a low dosage automatic injection system (Model ML 503A Dual Syringe Diluter, Hamilton, Nev.), and 6) a liquid evaporating chamber.

The hazardous gas used in the preferred embodiment of the present invention is 2-methoxy ethanol. The test concentration of the hazardous gas is 25 ppm in compliance with the allowable limit set forth by OSHA. In light of the lack of an exposure chamber large enough to accommodate a human body in its entirety, a small exposure chamber was used to investigate the absorption of the hazardous gas by the skin of an arm. On the basis of the result of the hand, the absorption of the hazardous gas by the skin of the whole body was estimated. Generally speaking, the arm of a male worker has a total area of 1,250 $cm^2$, whereas the total area of the whole body of the male worker amounts to 1.8 $m^2$ which is about 14.4 times the total area of the arm. A workwear can reduce the exposure of the male worker to the hazardous gas by 20–30%. The hand and the arm of a worker are often exposed on the job and are therefore used as subjects of the investigation. It is also assumed that the gas absorption rate of the skin of a hand is about equal to the average value of the gas absorption rate of the skin of the whole body. Such as assumption as described above is in fact underestimated. As a result, an absorbed dose of 300 ppm by a hand is about corresponding to an absorbed dose of 15 ppm by a whole body (300 ppm*1,250 $cm^2$/18,000 $cm^2$ 0.75). The upper and the lower limits of the hazardous gas concentration of the present invention was set at 25 ppm±1.5 ppm, which is corresponding to the concentration differential range of 6%. While the hand was exposed to the hazardous gas of 2-methoxy ethanol, the analog signals of the detector were continuously converted into the digital signals via an analog-to-digital converter (Model PPIO-08, Cyber Research Inc., New Haven, Conn.). The digital signals were then transmitted to a computer (Pentium 100). When the concentration signal of the hazardous gas contained in the exposure chamber received by the computer was lower than the lower limit of 23.5 ppm, an instruction was generated by the software program and transmitted to activate the automatic injection system to raise quickly the concentration up to the upper limit of 26.5 ppm. As a result, the concentration of the hazardous gas contained in the exposure chamber of the preferred embodiment of the present invention was well controlled so as to remain in the predetermined range of 23.5 ppm–26.5 ppm. The automatic injection system of the preferred embodiment of the present invention was completely controlled by the computer software. Throughout the experiment of the present invention, a series of injected doses of the hazardous gas were obtained. The sum of the injected doses was used to compute the absorbed dose of the hazardous gas by the skin.

The exposure chamber of the present invention is made of an electroplated polished stainless steel material so as to reduce the absorption of the organic gas by the wall of the exposure chamber. In addition, the exposure chamber is of an oval construction without corners capable of enhancing the mixing efficiency to improve the reaction time of the gas detection of the present invention. In addition, the exposure chamber of the present invention is externally connected with two small fans for promoting the evaporation of the liquid and enhancing the mixing effect to improve the reaction time of the detector. The rotation speeds of the two fans were adjusted to obtain desired wind velocities and flow streams by using an adjustable resistor. As shown in FIG. 1, a subject hand is located at the lower portion of the exposure chamber, whereas the injection, the evaporation, and the mixing are brought about in the upper portion of the exposure chamber. The wind velocity of the exposure chamber of the preferred embodiment of the present invention was measured by a hot-wire wind velocity meter (Alnor® AMP 360 multipurpose meter, Illinois). When the hand was extended into the exposure chamber, the contact portions of the hand and the exposure chamber were covered with two layers of aluminum foil in conjunction with a transparent plastic bag therebetween. In addition, the upper arm was banded with the 3M bandage to avert the gas leak. Located respectively in the front, the middle and the rear of the exposure chamber was a detector for monitoring the uniformity of the gas concentration distribution and the change in the gas concentration throughout the experiment. The exposure chamber of the preferred embodiment of the present invention had an inner volume of 43.77 liters.

Figure 2:
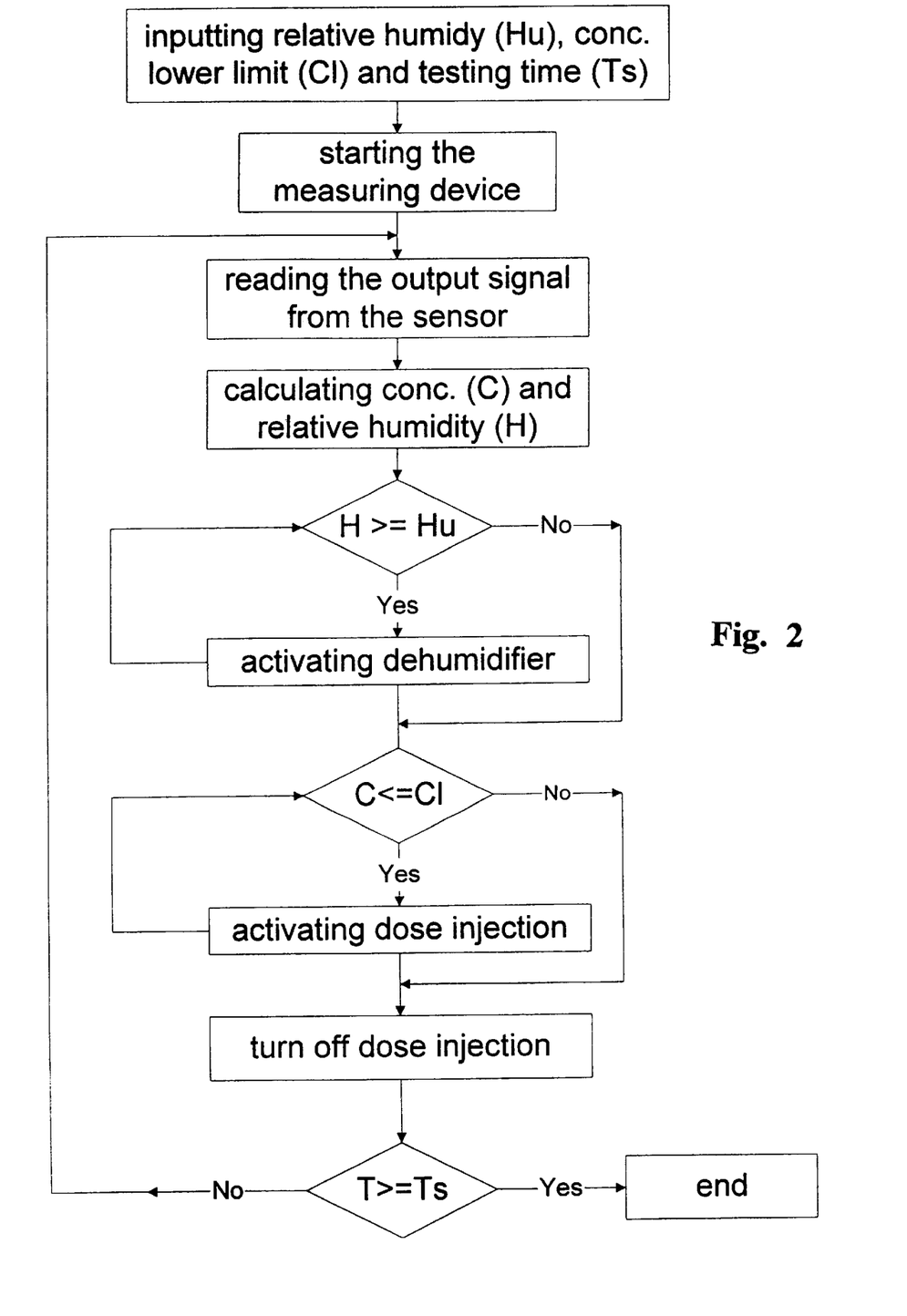
FIG. 2 shows a flow chart of a software program suitable for use in the present invention.

The software program of the preferred embodiment of the present invention was written by means of Microsoft® Visual Basic® version 4 for Window (Microsoft, U.S.A.). The flow chart of the entire program is shown in FIG. 2. The software program has an advantage in design in that it allows a user to operate the system with a mouse under the Microsoft® Window, and that various control parameters can be incorporated into the program prior to the operation. The parameters include the upper and the lower limits of the gas concentration, the volume of the exposure chamber, the test line parameters of the detectors, each injection dose, and the injection time. Throughout the experiment, the injection system and the dehumidifying system were controlled automatically by the software program such that the instant profiles of the concentration and the humidity of the exposure chamber and the data were displayed on the screen and stored in the computer. The changes in the concentrations of the three detectors were displayed on the upper left corner of the screen, thereby enabling the operator to use various colors to identify the concentration changes of the detectors. In addition, the instant data of a specific time can be indicated by the cursor such that the change can be observed at a desired time. The changes in the average concentration values of the three detectors are shown in the lower left corner of the screen. The injection dose and the accumulated injection doses were shown in the upper right corner of the screen. The changes in the temperature and the humidity were shown in the lower right corner of the screen. The figures of the instant monitor data were displayed in the left column of the screen.

The environmental factors, such as temperature, humidity, wind velocity, etc., can have a considerable impact on the signal output of the gas detector. In the present invention, the background humidity of the laboratory was 50–60%. When the hand was put into the exposure chamber, the humidity in the exposure chamber began to increase rapidly such that a thin layer of water was condensed on the wall having low temperature. In light of 2-methoxy ethanol which has an excellent water solubility, the 2-methoxy ethanol gas can easily dissolve in the condensed water. The output signal of the detector can be greatly influenced by the extremely high humidity. In order to avert such problems as described above, the inventors of the present invention used an impinger (SKC, No. 225-36-1, PA) connected with a cooling water bath (Model CH-603, Chin Hsin Inc., Taipei, Taiwan) as a cooling dehumidifying controller for emulating an actual working environment of high humidity, as shown in FIG. 1. The humidity of the exposure chamber was controlled by the temperature set by the cooling water bath and the sucking flow rate of the circulation pump. According to the data obtained from the experiment of the present invention, it is readily apparent that the system of the present invention is capable of an effective control of the relative humidity within 80±2%.

The room temperature was regulated by two air conditioners which were controlled by a microcomputer. The room temperature was set at 25±1° C. As soon as the hand was put into the exposure chamber, the temperature in the exposure chamber rose quickly to and remained at 27–28° C. The average wind velocity in the exposure chamber was 0.2–0.5 m/s, which was almost corresponding to the condition of the actual working site. The temperature-humidity in the exposure chamber was measured by a temperature-humidity meter (Model Humitter 50Y, Vaisala Inc., Woburn, Mass.).

The detectors used in the present invention included a gas phase chromatography (GC/FID, Varian 3400, CA), an infrared spectrometer (Miran IBX IR, Foxboro Inc., MA), and three tin oxide semiconductor detectors (Figaro Engineering Inc., Model TGS-822, Osaka, Japan; Futaba Electric Co., Model CS-6000-5cL, and CS-6000-3a, Hsinchu, Taiwan.) A Tedlar trapping bag (SKC, 232-20, Pennsylvania) of 40 liters was filled with a standard gas of a known concentration for use as a standard in the process of evaluating the detectors.

In light of the exposure chamber being a closed system, the sampling flow rate of the phase chromatography-ionic flame testing device was set at 1-2 mL/min, so as to reduce the consumption in quantity of the 2-methoxy ethanol gas by the testing device. The reaction time of the testing device was as long as 30 minutes due to the low pumping flow rate as well as the absorption by the walls of the connection pipe and the combustion chamber. As a result, it was unable to meet the requirement of the present invention and to provide the present invention with the instant and stable detection signal. The Miran IBX infrared spectrometer was abandoned in view of the fact that the output signal of the spectrometer contains noise, and that the output signal was unable to differentiate the upper and the lower limits of concentration in such a narrow control range of the present invention. After a number of tests, it was concluded that only the tin oxide semiconductor detectors were able to provide the present invention with a fast and stable signal output, as described in the following preparatory example 1.

In the process of evaluating the performances of the tin oxide ($SnO_2$) semiconductor detectors, a number of vital parameters were taken into account. The parameters include the intra-day stability of the signal output, the inter-day stability of the signal output, the reproducibility of sensor response between high and low concentrations, the response time of sensor, the background consumption of the hazardous gas, and the environmental factors such as temperature, humidity and wind velocity.

PREPARATORY EMBODIMENT 1

Performance Test of Tin Oxide Semiconductor Detectors

Figure 4:
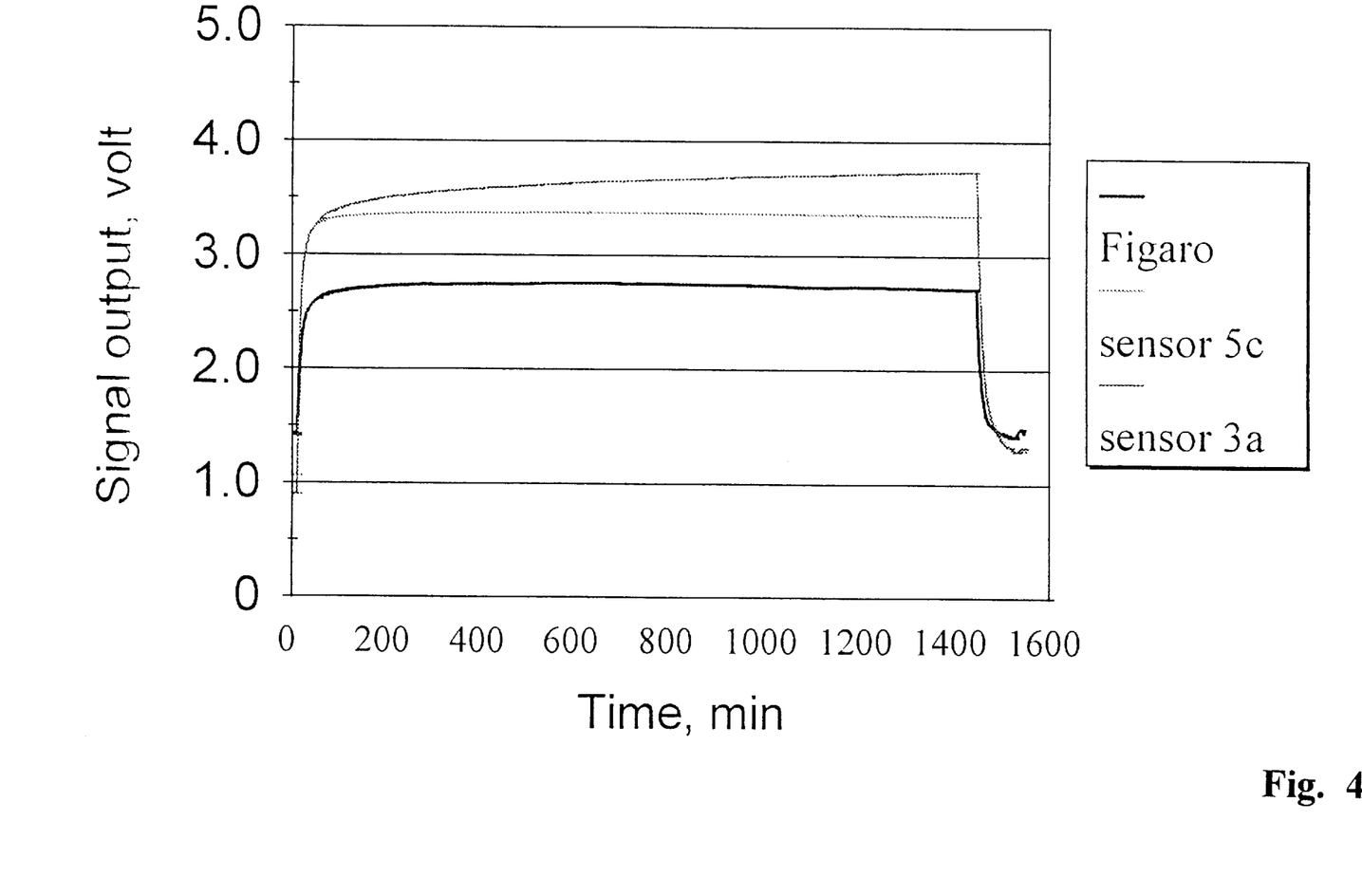
FIGS. 4–9 are time diagrams of the output voltage of the preparatory work of the preferred embodiment of the present invention as shown in FIG. 1.

As illustrated in FIG. 3, 25 ppm of the standard gas and the dry clean air were prepared by a trapping bag of 40 liters, in conjunction with a three-way valve. The results showed that Figaro TGS-822 detector and Futaba CS-6000-5cL detector were capable of attaining a stable intra-day signal output even after an uninterrupted use of up to 24 hours, as shown in FIG. 4. However, the output signals of Futaba-CS-6000-3a exhibited a gradual incremental pattern.

Figure 5:
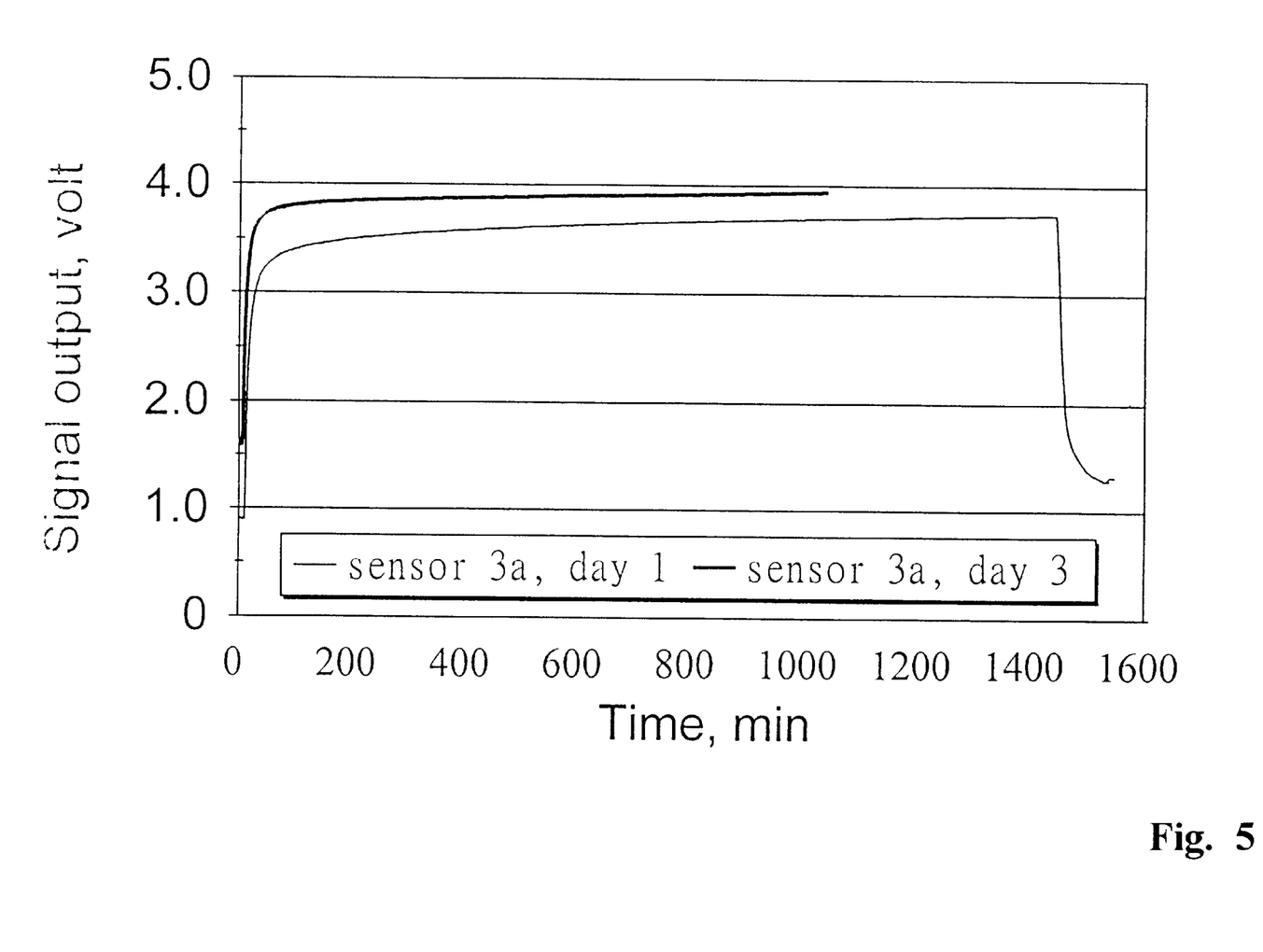
Figure 6:
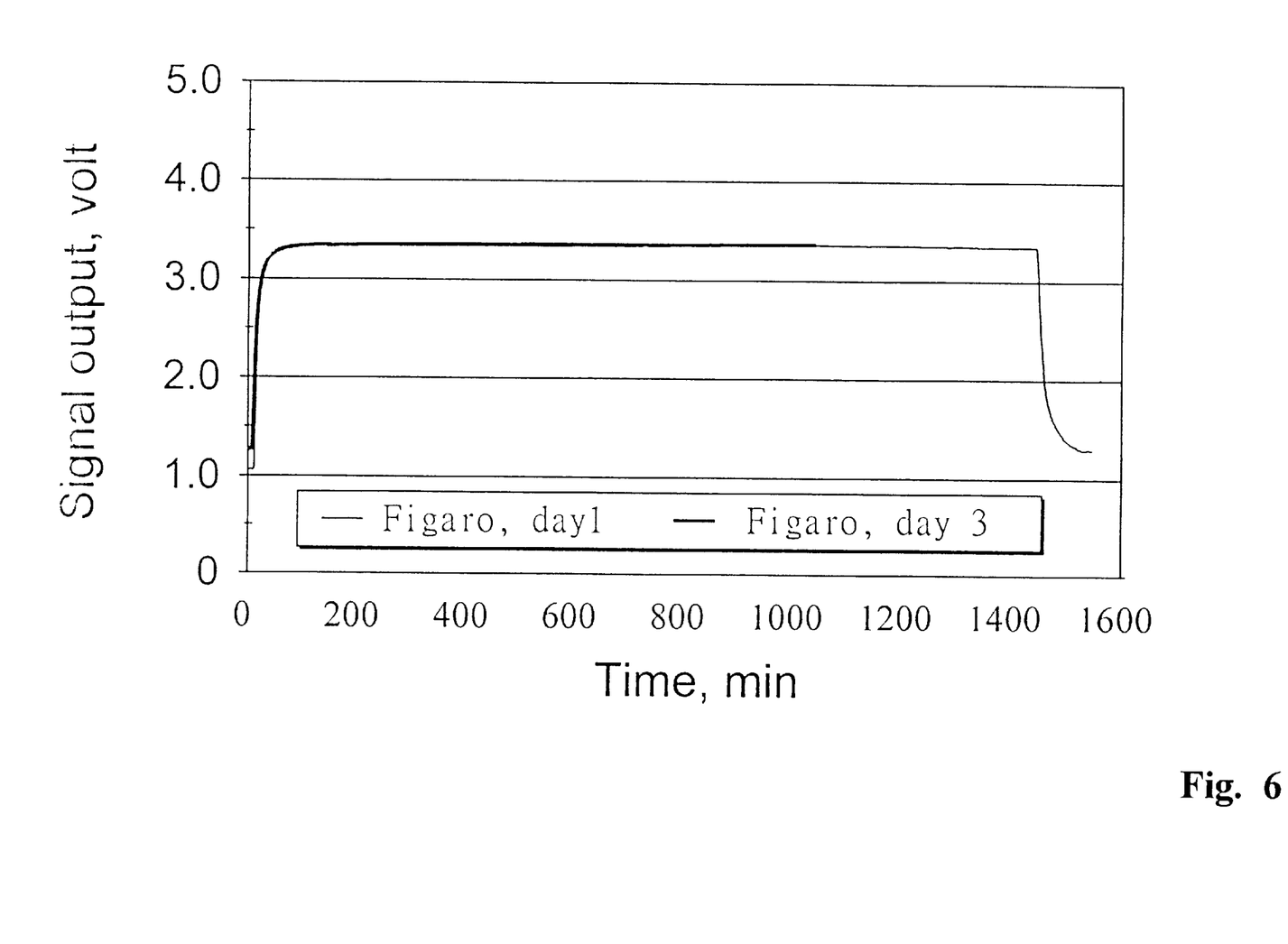
Figure 7:
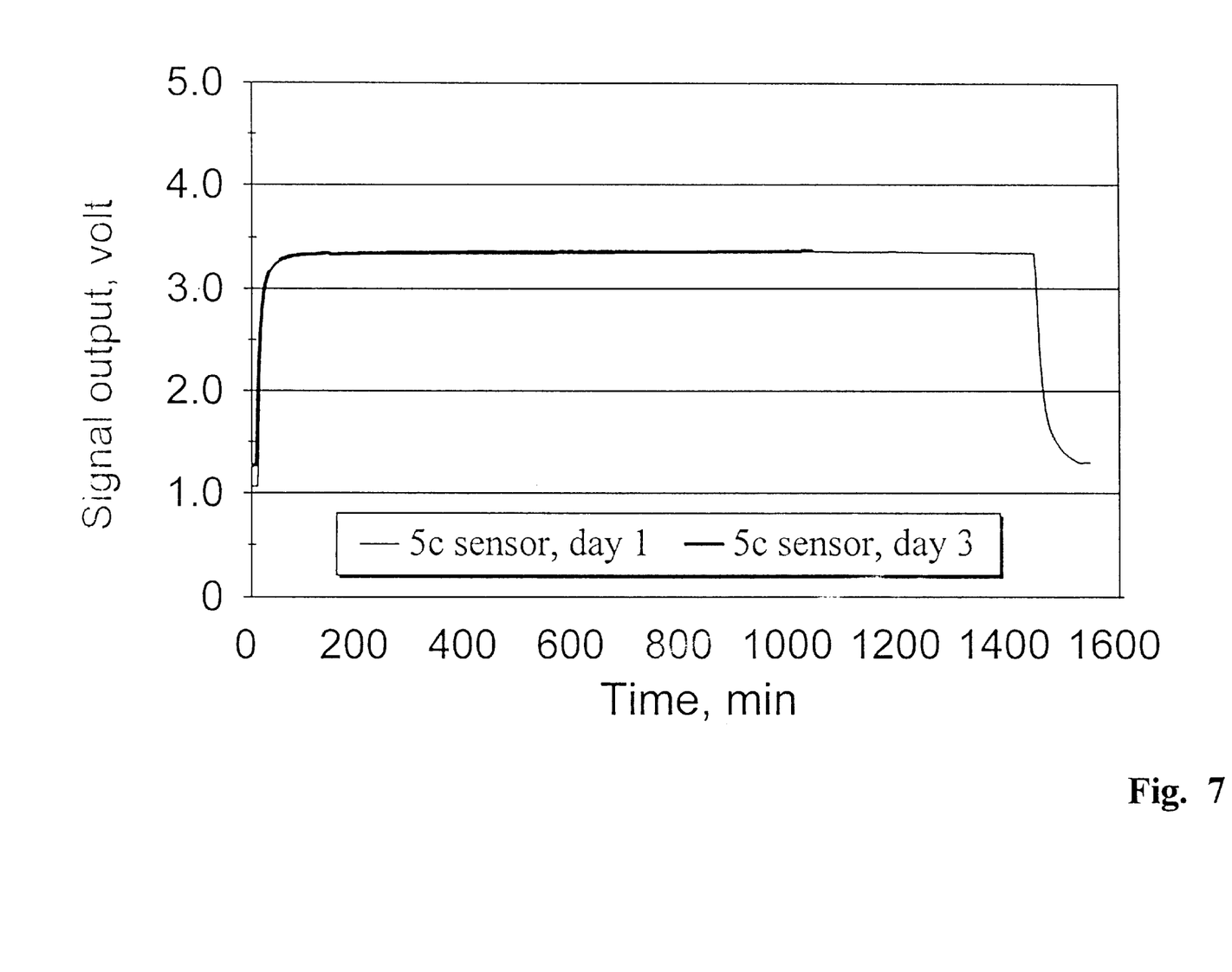

As shown in FIGS. 5–7, the inter-day output signals of Futaba-CS-6000-3a detector became stronger and more stable on the third day, whereas the inter-day output signals of Figaro TSG-822 detector and Futaba CS-6000-5cL detector were steady throughout the testing period.

Figure 8:
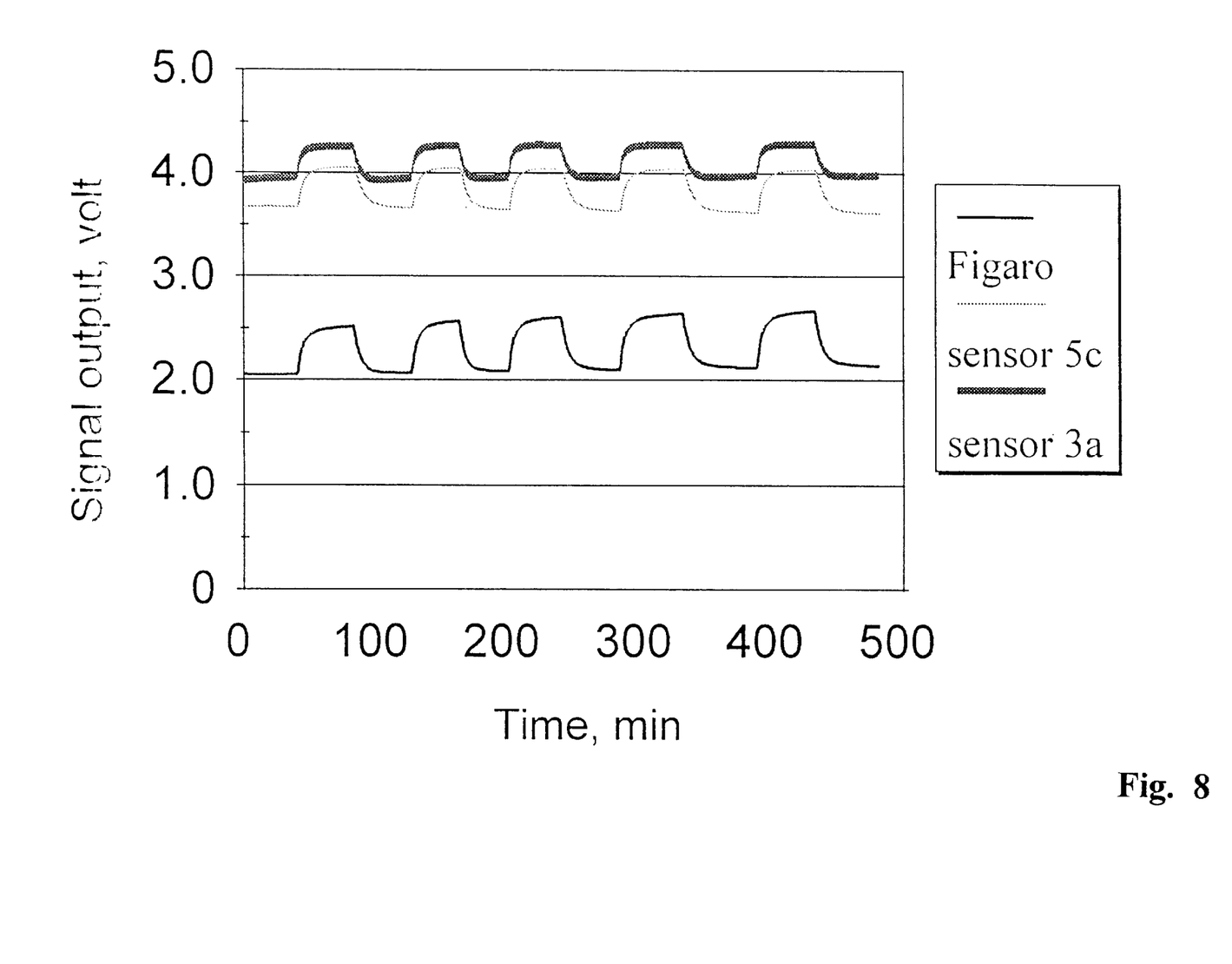

The reproducibility tests of the output signals were carried out by means of two 40-liter trapping bags and a three-way valve. The trapping bags were used to provide two standard gases (23.5 ppm and 26.5 ppm) of 2-methoxy ethanol. The switching of the concentration limits was attained by the three-way valve. As shown in FIG. 8, Futaba CS-6000-5cL detector was the best performer in the tests in which the concentrations were switched for fire consecutive times.

Figure 9:
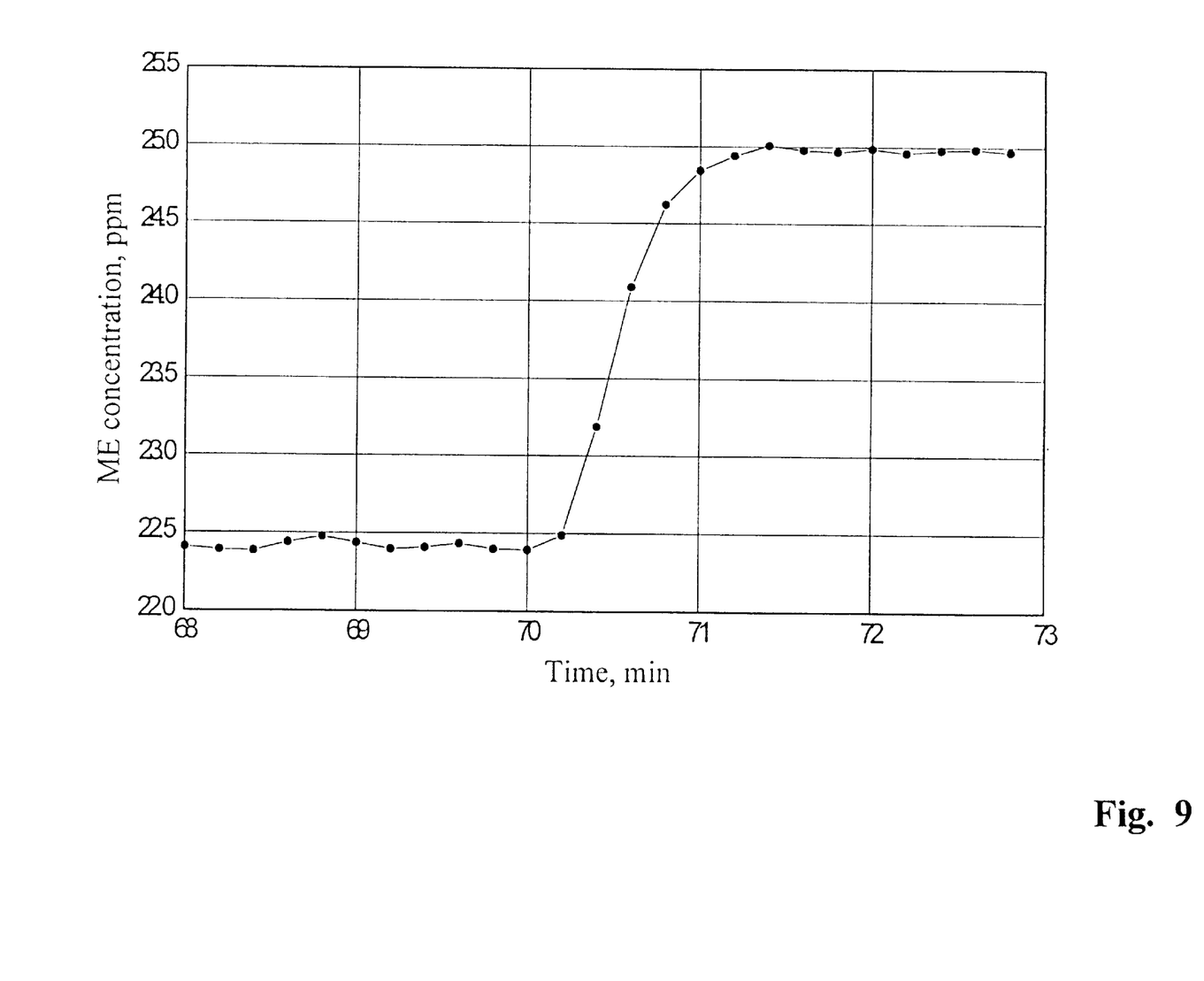

The response time of the detector is an important factor that must be taken into consideration in the test. The response time is generally expressed as $T_{90}$ and is the time which is required for a detector to attain 90% strength of its new equilibrium state from the base line value. As shown in FIG. 9, the response time ($T_{90}$) of Futaba CS-6000-5cL detector was shorter than 40 seconds from 22.5 ppm to 25 ppm. In FIG. 9, an interval between two dots represents 12 seconds. In the preparatory embodiment of the present invention, the Pentium 100 personal computer was capable of fetching the signals at the rate of 100 signals per second. This implies that each dot in FIG. 9 represents the average value of the 1200 output signals. As indicated in FIGS. 4–9, Futaba CS-6000-5cL detector exhibited the best performance of response time.

In light of Futaba CS-6000-5cL detector being an oxidation detector, it was necessary to carry out a test to understand the rate at which the 2-methoxy ethanol gas could be consumed by the detector in the course of the experiment. In addition, the test was carried out to understand the likelihood of an interfering oxide being produced in the course of the experiment. In the test, three Futaba CS-6000-5cL detectors were continuously operated in an exposure chamber for four hours. The test results showed that the concentration of the 2-methoxy ethanol gas contained in the exposure chamber decreased gradually and steadily from 26 ppm to 24.5 ppm. The likelihood of the concentration reduction due to the absorption by the wall of the exposure chamber was eliminated. For more details, please refer to the Preparatory Embodiment 3. Moreover, the repeated tests showed that the background consumption of the gas by the detectors was minimal and less than 1% of the total absorption, and could be took into account by deducting it from the measured concentration values. The detection of the interfering oxide was done by the phase chromatography (GC/MS, G1, 800A, GCD, Hewlett Packard, CA). No interfering oxide was found in the exposure chamber. The interference of impurities can be minimized by using the 2-methoxy ethanol gas of high purity.

The test results further showed that effect of the temperature on the performance of Futaba CS-6000-5cL detector was least possible when the detector was operated at the temperature ranging between 23° C. and 30° C. The room temperature of the laboratory was kept at 25±1° C. by two air conditioners which were controlled by a microcomputer. As a result, the temperature of the exposure chamber was kept stable at 27–28° C. It was thus concluded that the temperature effect could be legitimately ignored.

Figure 10:
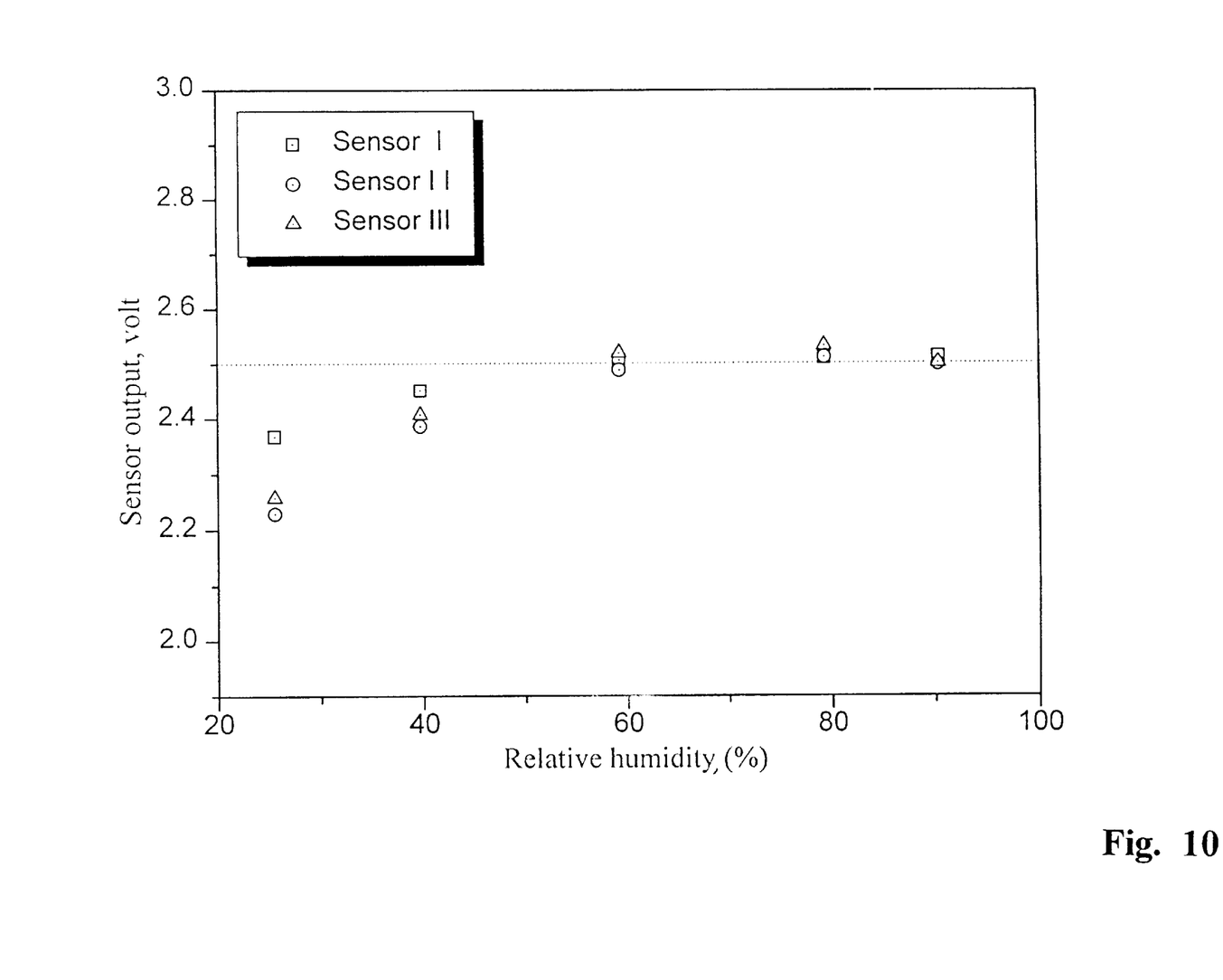
FIG. 10 shows a $T_{90}$ reaction time diagram of the preparatory work of the preferred embodiment of the present invention as shown in FIG. 1.

As shown in FIG. 10. the humidity effect on the performance of Futaba CS-6000-5cL detector was also proved to be minimal as long as the detector was performed at a relative humidity ranging between 60 and 90%. The humidity of the exposure chamber rose from 50–60% to 90% only 15 minutes after an arm was put into the exposure chamber. The increment of humidity was due to the skin perspiration of the arm. It was thus concluded that the humidity effect could be justifiably ignored.

Figure 11:
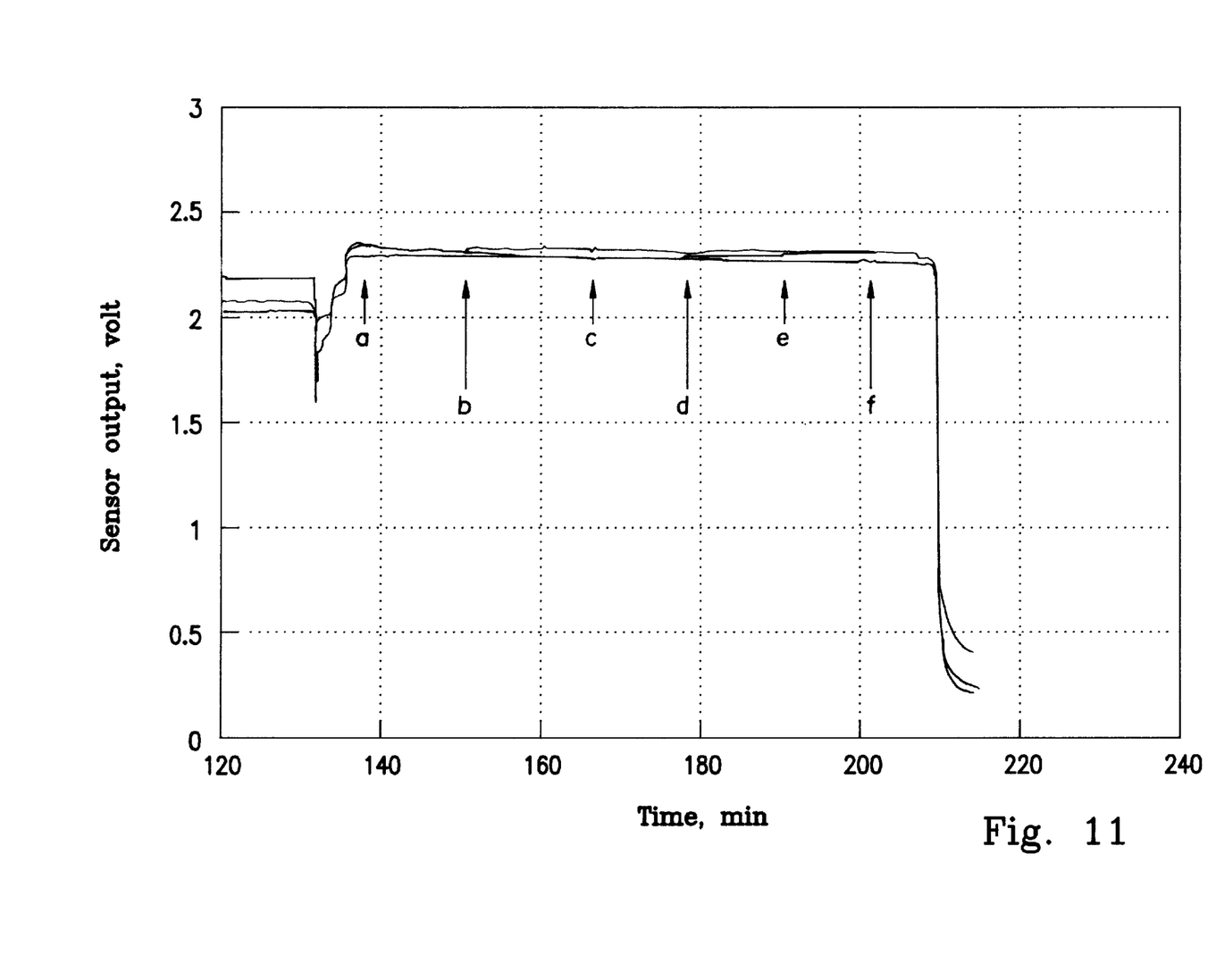
FIG. 11 shows a humidity effect diagram of the preparatory work of the preferred embodiment of the present invention as shown in FIG. 1.

As shown in FIG. 11, the effect of wind velocity on the performance of Futaba CS-6000-5cL detector was least possible at such time when the detector was operated at a wind velocity ranging between 0.2 and 1.2 m/s. The wind velocities at the points designated as a, b, c, d, e, and f are respectively 1.25 lpm (1.66 cm/s), 1.75 lpm (2.32 cm/s), 2.25 lpm (2.99 cm/s), 2.58 lpm (3.65 (cm/s), 3.25 lpm (cm/s), and 3.80 lpm (5.05 cm/s).

It is therefore readily apparent that the tests described above were carried out in the laboratory emulating the environment of a typical work place in terms of temperature (27±1° C.), humidity (80±2%), and wind velocity (0.2–1.2 m/s).

PREPARATORY EMBODIMENT 2

Evaluation of Performance of Exposure Chamber

The emphasis of the performance test of the exposure chamber was placed on the standard gas leak, the wall absorption of the standard gas, and the arrangement of the standard gas supply. The test was carried out by using the 2-methoxy ethanol standard gas of five different concentrations (19.6, 22.8, 26.0, 29.2, and 32.3 ppm). The standard gases were contained respectively in the exposure chamber and a 40-liter Tedlar trapping bag (SKC, 232-20, Pennsylvania). The standard gases were prepared by injecting a known quantity of 2-methoxy ethanol liquid into an evaporation chamber and blowing clean air into the trap while carrying the 2-methoxy ethanol vapor, as shown in FIG. 1. The flow rate of the diluted 2-methoxy ethanol vapor was calibrated by an infrared soap meter. The gas pumping was timed with precision by using a two-digit stop watch. The standard gas was released from the trapping bag after 30 minutes storage time. For each standard gas of a specific concentration, the gas pumping was carried out repeatedly with the same trapping bag for 3–5 times so as to make sure that the absorption by the wall of the trapping bag had reached a saturation point. In order to understand the wall absorption and the gas leak of the exposures chamber, the detector was installed in the exposure chamber right before and right after a four-hour storage time of the standard gas. The differences between the two output signals from the detector were compared.

As shown in Table 1, the standard gas of the trapping bag and the standard gas of the exposure chamber show no statistical deviation ($p > 0.88$, the relative percentage error of five concentrations being smaller than 8%). This implies that the wall absorption and the gas leak of the exposure chamber can be reasonably ignored.

If only the concentrations in the exposure chamber measured right before and right after the four-hour storage time were compared, it was found that there was no statistical deviation between the two concentrations, and that the relative percentage deviation of the two concentrations was smaller than 5%. This was a proof that neither the gas leak nor the wall absorption of gas took place. The response time ($T_{90}$) of the system was less than one minute when the 2-methoxy ethanol concentration was less than 25 ppm.

TABLE 1

| Exposure chamber | Trapping bag |
|---|---|
| 18.688 | 18.424 |
| 21.16 | 21.499 |
| 27.674 | 24.571 |
| 29.598 | 27.642 |
| 32.242 | 30.713 |

PREPARATORY EMBODIMENT 3

Calibration of Detector

Prior to the experiment, each detector was checked for the five-point concentration test line. The calibration concentrations ranged between about 20 and about 30 ppm. In light of the output signal of the detector and the concentrations being in a logarithmic linear relationship, the output voltages of the signals were expressed in watts, whereas the concentrations were entered as logarithm. Prior to each human experiment of the five-point concentration calibration, the relative humidity was first controlled at a fixed value. The exposure chamber was provided with a blind sample of an unknown concentration by a second chemist. The output signal of the detector was entered for the test line computation. The results showed that the coefficient (theoretical concentration/measured concentration) of the inter-day test lines was greater than 0.995, and that the relative percentage error of each concentration was smaller than 5%. The ANCOVA test showed that there was no statistical deviation ($0.2 > p > 0.1$) among the test line inclinations, as shown in Table 2.

TABLE 2

| | Theoretical Conc. (ppm) | 19.647 | 22.804 | 25.961 | 29.118 | 32.285 | |
|---|---|---|---|---|---|---|---|
| Day 1 | Voltage | 2.310 | 2.411 | 2.488 | 2.561 | 2.625 | Semi-log slope[3]: 1.452732 |
| | Measured Conc.[1] (ppm) | 19.647 | 22.975 | 25.887 | 28.987 | 32.008 | |
| | Conc. ratio[2] | 1.00 | 1.0075 | 0.9971 | 0.9955 | 0.9914 | |
| Day 2 | Voltage | 2.234 | 2.348 | 2.440 | 2.514 | 2.577 | Semi-log slope[3]: 1.590682 |
| | Measured Conc.[1] (ppm) | 19.647 | 23.443 | 27.034 | 30.319 | 33.427 | |
| | Conc. ratio[2] | 1.00 | 1.028 | 1.0413 | 1.0412 | 1.0354 | |
| Day 3 | Voltage | 2.285 | 2.391 | 2.472 | 2.543 | 2.604 | Semi-log slope[3]: 1.459872 |
| | Measured Conc.[1] (ppm) | 19.647 | 23.154 | 26.250 | 29.303 | 32.207 | |
| | Conc. ratio[2] | 1.00 | 1.0153 | 1.0111 | 1.0063 | 6.9976 | |
| Day 4 | Voltage | 2.201 | 2.306 | 2.393 | 2.466 | 2.525 | Semi-log slope[3]: 1.507544 |
| | Measured Conc.[1] (ppm) | 19.647 | 23.118 | 26.454 | 29.622 | 32.458 | |
| | Conc. ratio[2] | 1.00 | 1.0138 | 1.019 | 1.0173 | 1.0054 | |
| Day 5 | Voltage | 2.283 | 2.380 | 2.465 | 2.537 | 2.601 | Semi-log slope[3]: 1.476684 |
| | Measured Conc.[1] (ppm) | 19.647 | 22.833 | 26.047 | 29.122 | 32.157 | |
| | Conc. ratio[2] | 1.00 | 1.0013 | 1.0033 | 1.0001 | 0.996 | |
| Day 6 | Voltage | 2.383 | 2.497 | 2.567 | 2.638 | 2.695 | Semi-log slope[3]: 1.429012 |
| | Measured Conc.[1] (ppm) | 19.647 | 23.443 | 26.128 | 29.167 | 31.860 | |
| | Conc. ratio[2] | 1.00 | 1.028 | 1.0064 | 1.0017 | 0.9868 | |
| Day 7 | Voltage | 2.332 | 2.435 | 2.519 | 2.591 | 2.653 | Semi-log slope[3]: 1.487968 |
| | Measured Conc.[1] (ppm) | 19.647 | 23.047 | 26.250 | 29.348 | 32.307 | |
| | Conc. ratio[2] | 1.00 | 1.0106 | 1.0111 | 1.0079 | 1.0007 | |

[1] the measured concentrations were calculated from the voltages, wherein the voltage measured from the theoretical concentration of 19.647 was used as a basis.
[2] Conc. ratio = (Measured concentration)/(theoretical concentration).
[3] Semi-log slope was obtained from a log (measured concentration) vs. voltage plot.

PREPARATORY EMBODIMENT 4

Injection Rate Calibration of Injection System

The injection rate of the injection system was checked with a five-digit balance (Mettler model AT-201, Switzerland). 2-methoxy ethanol was continuously injected into a glass bottle, and six continuous injections were measured to obtain the average value and the coefficient of variation. Each continuous injection had 10 injection does. An average injection dose was obtained from the 50–100 injection doses. The average dose of each ejection was then used as a computation base for checking the injection dose of the system. After each human experiment, the above weight calibration was used again to check the average injection dose of each ejection so as to obtain the relative percentage error of the average injection doses before and after the experiment. The flash evaporation chamber is a small glass chamber which is embraced by a heating strap and a temperature control device, as shown in FIG. 1. The flash evaporation chamber was used to accelerate the evaporation of the liquid 2-methoxy ethanol and to shorten the reaction time of the system. When the evaporation of the liquid was slower than the skin absorption rate, it will cause the injection system to continuously inject the 2-methoxy ethanol, and thus result in an excess absorption dose of the vapor by the skin of the human under test. The flash evaporation chamber of the present invention can avoid this problem by providing with the heating strap.

The coefficient of variation of the injection doses of the micro-syringe was smaller than 2%. (The injection dose was set at 4 $\mu$L. Every ten injections were weighted.) The relative percentage error of 50 injections was smaller than 2%. The results were close to the specifications of the manufacturer, thereby suggesting that the injection system was stable and reliable.

The fast evaporation chamber shown in FIG. 1 was able to shorten the reaction time of the system from five minutes (without the heating strap) to 40 seconds, as shown in FIG. 9.

Management of Data

The test line relationship of the concentrations of 2-methoxy ethanol and the output signals of the detector was attained by the linear regression. The paired t-testing results and the relative percentage errors were used to compare:

1) the 2-methoxy ethanol mass captured by the activated carbon tube or the condensation dehumidifier with the total accumulated injection doses of the automatic injection system;

2) the differences between the output signals of the same detector in the exposure chamber and in the trapping bag, wherein five sets of the standard gas of the same concentration were respectively disposed in the exposure chamber and the trapping bag; and 3) the deviation between the mass weighed by the five-digit balance and the accumulated injection doses of the automatic injection system.

The deviation of concentrations in the exposure chamber before and after the four-hour storage time was expressed by the relative percentage error. The slope of the inter-day test lines were computed and analyzed by ANCOVA (Analysis of Covariance).

EMBODIMENT 1

Computation of Absorbed Dose of Vapor by Skin

The measurement of the absorbed dose of vapor by skin was carried out respectively with each of six voluntary subjects whose personal data are shown in the following Table 3:

TABLE 3

| Subject | Age | height (cm) | weight (kg) | surface area of subject's body* ($m^2$) |
|---|---|---|---|---|
| 1 | 27 | 174 | 85 | 2.00 |
| 2 | 28 | 170 | 65 | 1.75 |
| 3 | 30 | 174 | 69 | 1.83 |
| 4 | 36 | 168 | 78 | 1.88 |
| 5 | 23 | 180 | 75 | 1.94 |
| 6 | 23 | 170 | 66 | 1.77 |
| Average | | | | 1.86 |
| Standard deviation | | | | 0.10 |

*surface area of whole body was obtained by: $(weight)^{0.425} \times (height)^{0.725} \times 71.84$ The method of the first embodiment is illustrated in FIG. 1 in which the arm of a subject is shown being put into an exposure chamber. The exposure chamber contains 2-methoxy ethanol having a concentration of 300±10 ppm, with the relative humidity and the temperature of the exposure chamber being respectively 80±2%, and 25±1° C. For details of the control of the first embodiment, please refer to the Preparatory Embodiments described above. The results of the first embodiment are shown in the flowing Table 4.

TABLE 4

| Subject | $m_1$ (mg) | $m_2$ (mg) | $m_3$ (mg) | $m_4$ (mg) | Δm (mg) | exposed area ($cm^2$) | skin absorption rate ($\mu g/cm^2/h$) | permeability constant (cm/h) |
|---|---|---|---|---|---|---|---|---|
| 1 | 430.00 | 328.50 | 0.35 | 5.04 | 96.11 | 1,283.45 | 18.72 | 20.07 |
| 2 | 296.88 | 222.75 | 0.58 | 5.04 | 68.51 | 1,108.79 | 15.45 | 16.56 |
| 3 | 172.46 | 137.75 | 0.66 | 5.04 | 29.01 | 1,306.83 | 5.55 | 5.95 |
| 4 | 285.11 | 210.00 | 0.63 | 5.04 | 69.44 | 1,146.40 | 15.14 | 16.23 |
| 5 | 350.67 | 301.00 | 0.58 | 5.04 | 44.04 | 1,291.68 | 8.52 | 9.14 |
| 6 | 394.56 | 304.75 | 0.16 | 5.04 | 84.61 | 1,408.86 | 15.01 | 16.09 |
| Mean | | | | | 65.29 | 1,257.67 | 13.07 | 14.00 |
| sd | (Standard deviation) | | | | 24.97 | 111.03 | 4.96 | 5.31 |
| se | (standard error, $sd/n^{0.5}$) | | | | 10.20 | 45.33 | 2.02 | 2.17 |

EMBODIMENT 2

The second embodiment of the present invention is basically similar in design to the first embodiment of the present invention, except that 2-methoxy ethanol of the former has a concentration of 25±1.5 ppm, and that the results of the former are: m1=34.5mg; m2=27.1 mg; m3=0.04mg; m4=0.34mg; m5=trace.

The results of both first embodiment and second embodiment are consistent and suggestive of feasibility of the present invention.

The skin absorption rate, as shown in Table 2, is computed on the basis of an equation of R $(mg/cm^2/hr)=(m1-m2-m3-m4-m5)/(A*t)$, in which m1 is the accumulated doses added to stabilize the concentration in the exposure chamber; m2, the doses captured by the condensation dehumidifier; m3, the gas residual left on the exposed arm after the termination of exposure; m4, the consumption doses of three detectors in operation in the exposure chamber for four consecutive hours; m5, the doses contained in the subject's exhalations; A, the exposed area of the subject's skin; t, the exposure time. It must be noted here that m1 is equal to the post-calibration injection rate multiplied by the accumulated injection times. This inventor of the present invention discovered that m3 and m4 were respectively less than 1% of the dose of m1. The distribution coefficient of the human blood relative to air is as high as 32,836 (Johanson et al, 1988). According to the test results, the 2-methoxy ethanol doses in the subject's exhalation amounts to less than 0.4% of the total absorbed dose of 2-methoxy ethanol. According, m5 can be justifiably ignored. This implies that only m1 and m2 must be measured with precision. M1 is checked and obtained by the weight method, which is generally deemed as a first grade calibration standard. M2 is analyzed by the phase chromatography/mass spectrograph, which have been proved to be extremely reliable and accurate.

The system of the present invention has advantages over the prior art systems. The advantages of the present invention are explicitly described hereinafter.

The environmental factors, especially humidity, play an important role in determining the extent to which a hazardous gas is absorbed by the human skin. For example, the skin absorption of the chemical can increase by 50–200% (Johanson et al., 1991; Piotrowski, 1967; Mraz et al., 1992; Dutkiewicz, 1961) in an environment of high temperature and high humidity. The prior art techniques are generally unable to account for the extent to which the environmental factors of temperature and humidity are controlled. In order to overcome such a technical deficiency of the prior art technology, the present invention is provided with an automatic feedback exposure chamber, a condensation dehumidifier and an air conditioner for emulating a work place environment in terms of relative humidity (80±2%), exposure concentration (25±0.5 ppm or 300±10 ppm), and exposure temperature (25±1° C.). In other words, the present invention is the first of its kind to provide the direct instant measurement technique.

The measuring technique of the present invention is humanized such that the skin absorption of the hazardous gas is measured directly without having to take a biological sample from the subject, such as blood, urine, and so forth. The present invention is capable of minimizing the base effect and the analytical interference.

The system of the present invention allows a short-term and a long-term evaluations of the skin absorption rate of the hazardous gas. As a result, the present invention can be used to provide more accurate and precise dynamics information if the present invention is combined with the biological detection techniques. In other words, the present invention is capable of providing a better understanding as to the absorption, the distribution and the metabolism of the hazardous gas in the human body.

The system of the present invention is relatively cost-effective and efficient than the dynamic standard gas generator of the prior art. In addition, the present invention is more accurate and precise in performance as compared with the prior art systems. This is particularly true with the situation in which the evaluation of the skin absorption of the non-polar hazardous substance is involved. The non-polar hazardous substance has a relatively low water solubility and is therefore less likely to be trapped by the condensed water. Both hardware and software of the system of the present invention can be economically set up. In addition, the system of the present invention is neither labor-intensive nor time-consuming.

What is claimed is:

1. A device for measuring an absorbed dose of gas by skin, said device comprising:

an exposure chamber for containing the gas to be measured and for containing a limb to be exposed to the gas;

a gas concentration control system connected with said exposure chamber for controlling a concentration of the gas within a predetermined range; and a gas sensor, said gas sensor being disposed in said exposure chamber for detecting the concentration of the gas such that a concentration signal is transmitted to said gas concentration control system.

2. The device as defined in claim 1 further comprising a temperature sensor and a temperature control unit for controlling temperature of said exposure chamber, said temperature control unit being an integral part of said gas concentration control system.

3. The device as defined in claim 2 further comprising a relative humidity sensor and a humidity control unit for controlling humidity of said exposure chamber, said humidity control unit being an integral part of said gas concentration control system.

4. The device as defined in claim 1, wherein said gas is a compound containing a hydroxyl group; and wherein said gas sensor is hydroxyl-group sensor.

5. The device as defined in claim 4, wherein said gas is a vapor of an alcohol.

6. The device as defined in claim 5, wherein said gas is 2-methoxy ethanol vapor.

7. A method for measuring an absorbed dose of gas by skin, said method comprising the steps of:

(a) putting a limb containing skin into an exposure chamber such that said exposure chamber is hermetically sealed;

(b) controlling concentration of a hazardous gas contained in said exposure chamber such that said concentration is kept in a predetermined range, wherein an amount of said hazardous gas is injected into said exposure chamber when said concentration drops below said predetermined range until said concentration is once again kept in said predetermined range; and (c) computing an absorbed dose of said hazardous gas by the skin of said limb from said amount of said hazardous gas injected.

8. The method as defined in claim 7, wherein the step (b) further comprises a control of temperature of said exposure chamber.

9. The method as defined in claim 8, wherein the step (b) further comprises a control of relative humidity of said exposure chamber.

10. The method as defined in claim 7, wherein said hazardous gas is a compound containing a hydroxyl group.

11. The method as defined in claim 10, wherein said hazardous gas is a vapor of an alcohol.

12. The method as defined in claim 11, wherein said alcohol is 2-methoxy ethanol.

* * * * *